US00PP32253P3

(12) United States Plant Patent
Rimland

(10) Patent No.: US PP32,253 P3
(45) Date of Patent: Sep. 29, 2020

(54) ***ZAMIOCULCAS ZAMIIFOLIA* PLANT NAMED 'CHAMELEON'**

(50) Latin Name: *Zamioculcas zamiifolia*
Varietal Denomination: Chameleon

(71) Applicant: Michael Kerry Rimland, Miami, FL (US)

(72) Inventor: Michael Kerry Rimland, Miami, FL (US)

( * ) Notice: Subject to any disclaimer, the term of this patent is extended or adjusted under 35 U.S.C. 154(b) by 0 days.

(21) Appl. No.: 16/350,872

(22) Filed: Jan. 28, 2019

(65) Prior Publication Data

US 2020/0245520 P1 Jul. 30, 2020

(51) Int. Cl.
*A01H 5/12* (2018.01)

(52) U.S. Cl.
USPC ..... Plt./373

(58) Field of Classification Search
USPC ..... Plt./373
CPC ..... A01H 5/12; A01H 5/00
See application file for complete search history.

*Primary Examiner* — Keith O. Robinson
(74) *Attorney, Agent, or Firm* — J. Wiley Horton

(57) ABSTRACT

A new and distinct *Zamioculcas zamiifolia* cultivar named 'Chameleon' is disclosed, characterized by variegated and metachromatic leaves that change in color from yellow, to yellow with green veins and tips, to green. The new variety is a *Zamioculcas zamiifolia*, normally produced as an ornamental plant.

3 Drawing Sheets

Latin name of the genus and species of the plant claimed: *Zamioculcas zamiifolia.*

Varietal, denomination: 'Chameleon.'

BACKGROUND OF THE INVENTION

The present invention relates to a new and distinct cultivar of *Zamioculcas*, botanically known as *Zamioculcas zamiifolia*, and hereinafter referred to by the name 'Chameleon.'

The new, spontaneous mutuation of the *Zamioculcas* plant cultivar was discovered by Michael Kerry Rimland in November 2017 in a plant nursery in Bangkok Thailand. Asexual reproduction of the 'Chameleon' by vegetative cuttings was first performed in January 2018 and has shown that the unique features of this cultivar are stable and reproduced true to type in successive generations of asexual reproduction.

SUMMARY OF THE INVENTION

The cultivar 'Chameleon' has not been observed under all possible environmental conditions. The phenotype may vary somewhat with variations in environment such as temperature, day length, and light intensity without, however, any variance in genotype.

The following traits have been repeatedly observed and are determined to be the unique characteristics of 'Chameleon.' These characteristics in combination distinguish 'Chameleon' as a new and distinct *Zamioculcas zamiifolia* cultivar:

1. Variegated leaves.
2. Metachromatic leaves.

Plants of 'Chameleon' can be compared to plants of the parent selection, *Zamioculcas zamiifolia*. However, 'Chameleon' differs from the plants of the mutation parent selection in the following characteristics:

1. Plants of 'Chameleon' produced variegated leaves that are yellow with green veins and tips.

2. Plants of 'Chameleon' produced leaves that change from a solid yellow to a solid green color.
3. Plants of 'Chameleon' display green, yellow, and/or variegated leaves all at once.

Plants of the new *Zamioculcas* can be compared to plants of the *Zamioculcas zamiifolia* 'LUCKYWHIT,' disclosed in U.S. Plant Pat. No. 23,614. In side-by-side comparisons, however, the new *Zamioculcas* differs from plants of 'LUCKYWHIT' in the following characteristics:

1. Plants of 'Chameleon' not only displayed variegated leaves, but also displayed pure green and pure yellow leaves at once.
2. Plants of 'Chameleon' produce metachromatic leaves that change in color from yellow, to variegated green and yellow, to green.

BRIEF DESCRIPTION OF THE PHOTOGRAPHS

The accompanying colored photographs illustrate the overall appearance of the new *Zamioculcas* showing the colors as true as it is reasonably possible to obtain in color reproductions of this type, Colors in the photograph may differ slightly from the color values cited in the detailed botanical description of the new variety which accurately describes the colors of the new *Zamioculcas* plant.

DETAILED BOTANICAL DESCRIPTION OF THE NEW VARIETY

Figure 1:
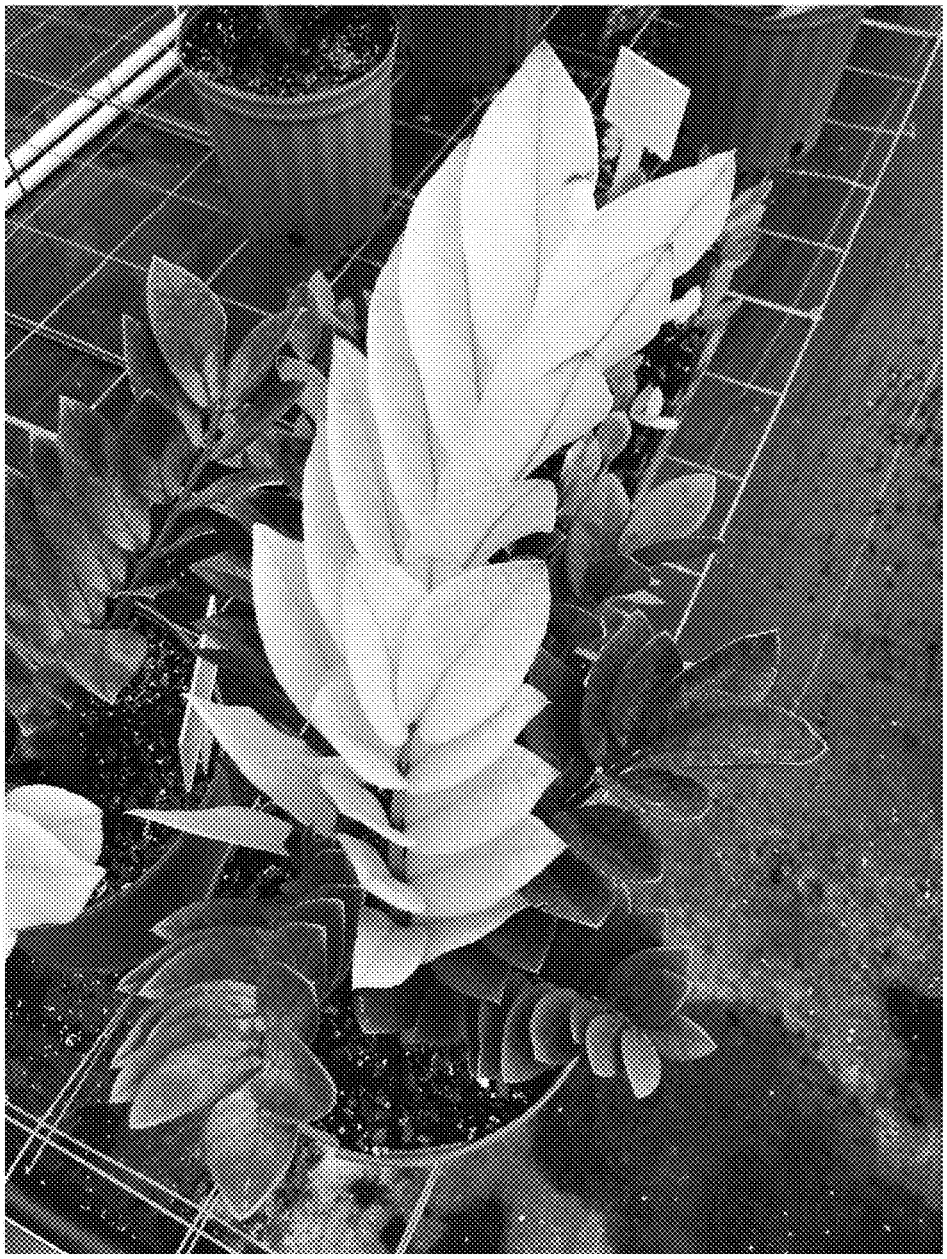
FIG. 1 is a side perspective view of a typical plant of 'Chameleon,' illustrating a branch with leaves that have yet to change color.
Figure 2:
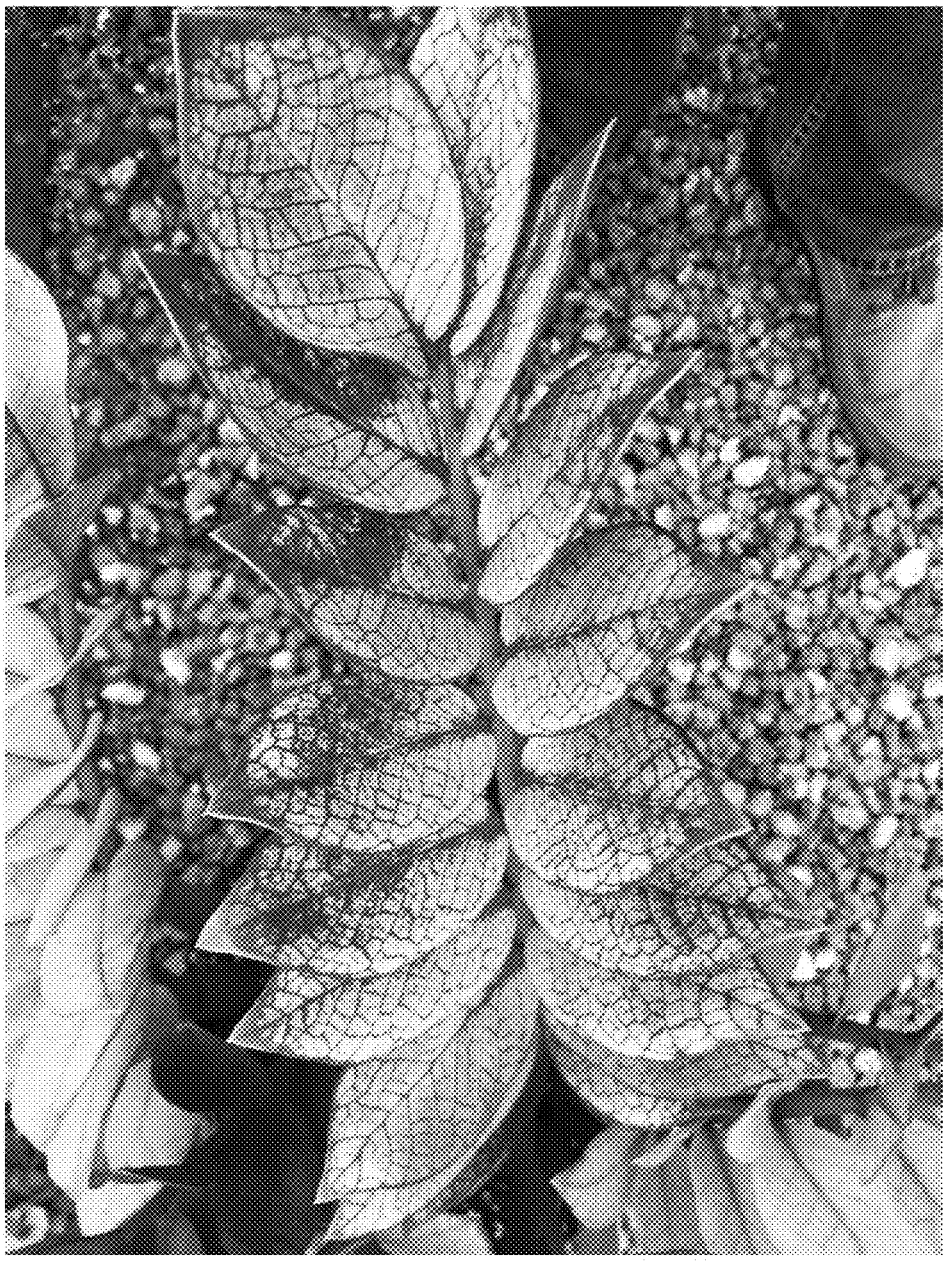
FIG. 2 is a close-up view of a typical branch of 'Chameleon,' illustrating variegated leaves as they are changing in color from yellow to green.
Figure 3:
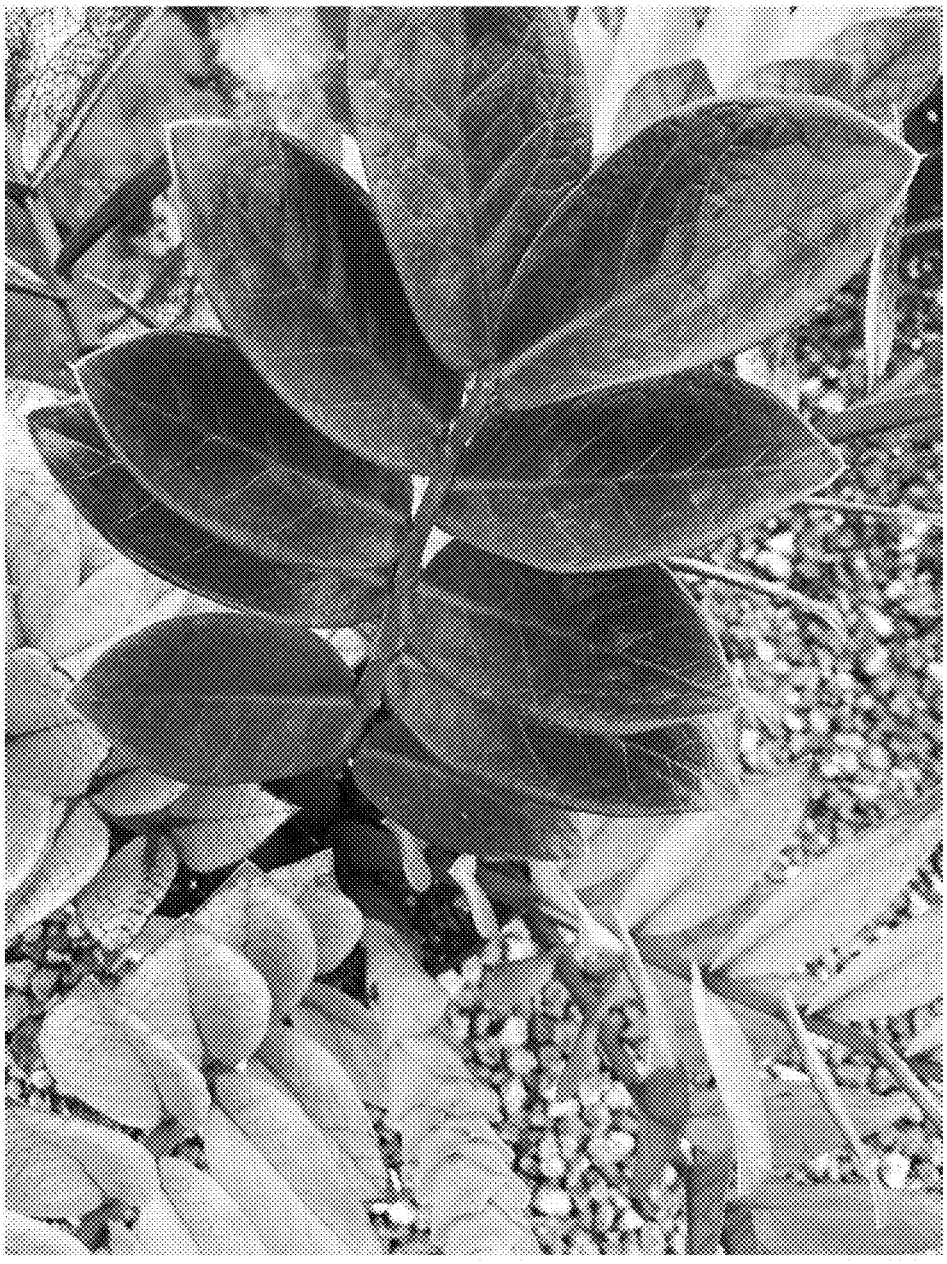
FIG. 3 is a perspective view of a typical plant of 'Chameleon,' illustrating branches with green, variegated, and yellow leaves at once.

The aforementioned photographs and the following observations, measurements, and values describes plants of the new *Zamioculcas* were grown in Homestead, Fla., United States in a shade house during the spring, summer and fall in 10.16 cm containers and under cultural practices types of commercial *Zamioculcas* production. During the production of the plants, temperatures ranged from about 13 degrees to 35 degrees Celsius and light levels were normal sunlight.

Plants were growing about 3-11 months when the photographs and the description were taken. However, it should be noted that the cultivar 'Chameleon' can grow up to 76-cm tall, maybe taller given time, if grown in larger pots. Even at this height, the characteristics of the 'Chameleon' as described remain true.

The following is a detailed description of the new plant characteristics with color in terminology in accordance with The Royal Horticultural Society Colour Chart, Edition V (2007), except where ordinary dictionary significance of color is indicated.

Botanical classification: *Zamioculcas zamiifolia* 'Chameleon.'

Propagation:

*Typical.*—By vegetative leaf cuttings.

*Time to initiate roots, summer.*—About 3 weeks at temperatures of 21 degrees to 35 degrees Celsius.

*Time to initiate roots, winter.*—About 4 weeks at temperatures of 15 degrees to 29 degrees Celsius.

*Time to produce a rooted young plant, spring/summer.*—About 22 weeks at temperatures of 21 degrees to 35 degrees Celsius.

*Root description.*—Free branching and dense. Fleshy when plants mature and white to light brown in color. Medium to thick in thickness.

Plant:

*Growth habit.*—Upright, compact, narrow inverted triangular, stemless, low to moderately vigorous, compact leaves in loose basal rosettes. Appropriate for 8.5 cm or larger containers.

*Plant shape.*—Whole plant narrow inverted triangular shape.

*Height.*—Approximately 25 cm to top of highest leaf.

*Plant spread.*—Approximately 15 cm in a 15 cm pot.

*Growth rate.*—Moderate.

*Branching characteristics.*—Non-branching, leaves grow directly from a basal clump.

*Number of clumps.*—About 2-3 per plant.

*Number of leaves per clump.*—About 3-6 leaves.

*Age of plant described.*—Approximately 9 months.

Foliage:

*Leaf.*—Pinnately compounded, about 3-6 leaves per basal rosette, each with 12-24 leaflets. Leaflets have short petiolules (about 4-5 mm in length and about 2 mm in diameter). Petiolules are medium to strong and smooth. Leaves are about 3 cm in width. Petiole diameter at base is about 4 mm and length is about 19 mm. Petiole diameter at the lowermost leaflet is about 6 mm.

*Leaflet.*—Obtuse shape, rounded base, apex is acute. Average length is 5 cm and average width is about 2.5 cm. Very glossy and smooth texture on the top surface, glabrous and matte on the bottom surface. Color ranges from bright yellow 2C, to light green 149D, to deep green 135B. Color is the same on upper and under side. Margin is entire, without serration.

*Venation.*—Pinnate type. Color ranges from a yellow-green 1491D to green 142A and changes over time due to metachromatic nature of 'Chameleon.' Color is the same on upper and under side.

*Rachis.*—Length is approximately 50 cm. Width at narrowest point is approximately 0.30 cm and above clump is approximately 1.90 cm. Very strong in strength, smooth, dull, glabrous texture. Near yellow-green 149D in color.

*Stipules.*—Inconspicuous or entirely absent (exstipulate).

*Other structures.*—None present.

Flower: Flower development has not been observed. No reproductive organs have been observed. Typically, non-flowering.

Other characteristics:

*Seed production.*—No seed production to date has been observed.

*Disease resistance.*—Neither resistance nor susceptibility to diseases or pests have been observed in this variety.

*Drought tolerance.*—Moderate tolerance for drought.

*Temperature tolerance.*—Low temperature tolerance to at least 7 degrees Celsius, high temperatures to at least 38 degrees Celsius.

*Other distinctive characteristics.*—Overall commercially interesting appearance. Metachromatic leaves that change in color from yellow, to variegated yellow with greens veins, to green over the course of about one month. At once, the 'Chameleon' may display all color variations described herein.

What is claimed is:

1. A new and distinct cultivar of *Zamioculcas zamiifolia* plant named 'Chameleon' as illustrated and described.

* * * * *